(12) United States Patent
Hurst et al.

(10) Patent No.: US 9,040,096 B2
(45) Date of Patent: May 26, 2015

(54) JASMONIC ACID COMPOUNDS IN COCOA PRODUCTS

(75) Inventors: William Jeffrey Hurst, Mt. Gretna, PA (US); David A. Stuart, Hershey, PA (US); Angela Isabel Calderon Justavino, Auburn, AL (US); Richard B. Van Breemen, Elmhurst, IL (US)

(73) Assignee: The Hershey Company, Hershey, PA (US)

( * ) Notice: Subject to any disclaimer, the term of this patent is extended or adjusted under 35 U.S.C. 154(b) by 608 days.

(21) Appl. No.: 13/061,300

(22) PCT Filed: Aug. 27, 2009

(86) PCT No.: PCT/US2009/055119
§ 371 (c)(1),
(2), (4) Date: Jul. 5, 2011

(87) PCT Pub. No.: WO2010/025209
PCT Pub. Date: Mar. 4, 2010

(65) Prior Publication Data
US 2011/0257263 A1     Oct. 20, 2011

Related U.S. Application Data

(60) Provisional application No. 61/092,506, filed on Aug. 28, 2008.

(51) Int. Cl.
| *A61K 36/185* | (2006.01) |
| *C12N 9/99* | (2006.01) |
| *A23G 1/48* | (2006.01) |
| *A23G 1/56* | (2006.01) |
| *A23L 1/30* | (2006.01) |
| *C07C 303/24* | (2006.01) |

(52) U.S. Cl.
CPC .. *C12N 9/99* (2013.01); *A23G 1/48* (2013.01); *A23G 1/56* (2013.01); *A23G 2200/14* (2013.01); *A23L 1/3002* (2013.01); *C07C 303/24* (2013.01)

(58) Field of Classification Search
USPC .......................................................... 424/776
IPC .......................................... A61K 36/18,36/185
See application file for complete search history.

(56) References Cited

U.S. PATENT DOCUMENTS

| 6,458,569 B1* | 10/2002 | Farbood et al. ............... 435/148 |
| 6,469,061 B1 | 10/2002 | Flescher |
| 2003/0157207 A1 | 8/2003 | Hammerstone, Jr. et al. |
| 2005/0043178 A1 | 2/2005 | Vivanco et al. |
| 2008/0131565 A1* | 6/2008 | Kealey et al. ................... 426/93 |
| 2008/0268097 A1* | 10/2008 | Hurst et al. ..................... 426/45 |

OTHER PUBLICATIONS

Kilaru et al. FEMS Microbiol. Lett. 2007 (furst published online Jul. 5, 2007). vol. 274, pp. 238-244.*
Jae B. Park, Caffedymine from Cocoa Has COX Inhibitory Activity Suppressing the Expression of a Platlet Activation Market, P-Selectin, Journal of Agricultural and Food Chemistry, 2007, vol. 55, pp. 2171-2175.
Richard A. Dixon, Natural products and plant disease resistance, Nature, vol. 411, Jun. 14, 2001, pp. 843-847.
Eliezer Flescher, Jasmonates in cancer therapy, Cancer Letters 245 (2007) pp. 1-10.
Philippe Reymond and Edward E. Farmer, Jasmonate and salicylate as global signals for defense gene expression, Plant Biology, 1998, 1:404-411.
Bryan A. Bailey, Mary D. Strem, Hanhong Bae, Gabriela Antunez De Mayolo, Mark J. Guiltinan, Gene expression in leaves of *Theobroma cacao* in response to mechanical wounding, ethylene, and/or methyl jasmonate, Plant Science 168 (2005) pp. 1247-1258.
Alessandra Devoto, John G. Turner, Regulation of Jasmonate-mediated Plant Responses in *Arabidopsis*, Annals of Botany, 92, 2003, pp. 329-337.
Gildemberg Amorim Leal Jr, Paulo S. B. Albuquerque, Antonio Figueira, Genes differentially expressed in *Theobroma cacao* associated with resistance to witches' broom disease caused by *Crinipellis perniciosa*, Molecular Plant Pathology (2007) 8 (3), pp. 279-292.
Joseph A. Verica, Siela N. Maximova, Mary D. Strem, John E. Carlson, Bryan A. Bailey, Mark J. Guiltinan, Isolation of ESTs from cacao (*Theobroma cacao* L.) leaves treated with inducers of the defense response, Plant Cell Rep (2004) 23:404-413.
Xianchun Li, mary A. Schuler, May R. Berenbaum, Jasmonate and salicylate induce expression of herbivore cytochrome P450 genes, Nature, Oct. 2002, vol. 419, pp. 712-715.
Mats Hamberg, Ana Sanz, Maria Josefa Rodriguez, Angel Pablo Calvo, Carmen Castresana, Activiation of the Fatty Acid a-Dioxygenase Pathway during Bacterial Infection of Tobacco Leaves, The Journal of Biological Chemistry, vol. 278, No. 51, Dec. 19, 2003, pp. 51796-51805.
Eliezer Flescher, Anti-Cancer Drugs: Jasmonates—a new family of anti-cancer agents, Oct. 2005, vol. 16, Issue 9, 911-916 (Abstract).
Robert E. King, Joshua A. Bomser, David B. Min, Bioactivity of Resveratrol, Comprehensive Reviews in Food Science and Food Safety, vol. 5, 2006, pp. 65-70.
Gidda, Satinder et al., Biochemical and Molecular Characterization of a Hydroxyjasmonate Sulfotransferase from *Arabidopsis thaliana*, The Journal of Biological Chemistry (2003), vol. 278, No. 20, May Issue, 17895-17900.
International Search Report and Written Opinion issued in PCT/US2009/055119, dated Oct. 20, 2009.
Minifie, B.W.; Chocolate, Cocoa, and Confectionery, 3d Edition, Aspen Publishers, Gaithersburg, Maryland, 1991, chapter 2 Cocoa Processes.

* cited by examiner

*Primary Examiner* — Chris R Tate
(74) *Attorney, Agent, or Firm* — David Kulik

(57) ABSTRACT

The invention provides methods for isolating and enhancing the levels of jasmonates from cacao plant sources. In a preferred embodiment, jasmonic acid and 12-hydroxy jasmonate sulfate are detected in various cocoa products, and the levels of these compounds can be manipulated to increase the beneficial health effects of a food product made with the cocoa products The invention includes methods to prepare edible products containing cocoa jasmonates.

4 Claims, 2 Drawing Sheets

JASMONIC ACID COMPOUNDS IN COCOA PRODUCTS

RELATED APPLICATION

This application claims priority to U.S. Provisional Application No. 60/092,506, filed Aug. 28, 2008. The above-listed prior application is specifically incorporated herein by reference in its entirety.

FIELD OF THE INVENTION

The invention relates to compositions comprising jasmonate compounds derived from cacao plant materials. More specifically, in one aspect the invention relates to cocoa ingredients having detectable levels of 12-hydroxy jasmonate sulfate and methods of making cocoa ingredients having this and other jasmonate compounds.

RELEVANCE OF THE INVENTION AND DESCRIPTION OF RELATED ART

Jasmonic acid compounds, or jasmonates, have been identified in numerous plants and are thought to regulate stress responses in plants. Some of these compounds, especially methyl jasmonate and its halogenated derivatives, have been studied and used for human therapy (see, for example, Flescher, "Jasmonates in cancer therapy," Cancer Letters 245:1-10 (2007)). To date, however, these compounds have not been described or isolated from *Theobroma cacao* plants or cocoa products.

BRIEF SUMMARY OF THE INVENTION

Figure 1:
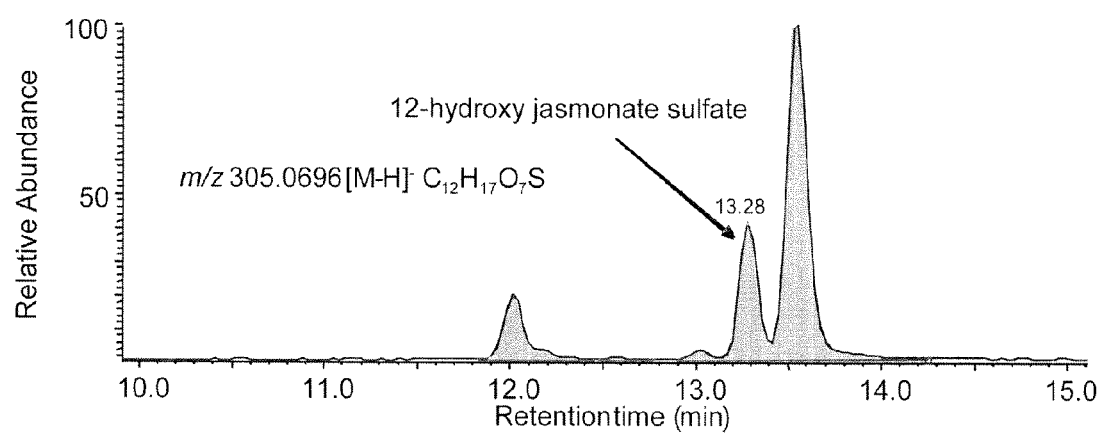
FIG. 1 depicts constituents from cocoa powder detected at m/z 305 using negative ion LC-MS including the detection of 12-hydroxy jasmonate sulfate at a retention time of 13.3 min. Accurate mass measurement is obtained using a high resolution LTQ FT ICR mass spectrometer at a resolving power of 200,000, and the elemental composition was confirmed to be $C_{12}H_{17}O_7S$ (0.3 ppm of the theoretical mass of 305.0695).

The invention relates to methods for isolating and detecting jasmonates in cocoa products and plant material from *Theobroma cacao*. Surprisingly, the compound 12-hydroxy jasmonate sulfate has been found in relatively high levels in cacao plant products, on a level that the known proanthocyanidin A2 compound has been detected. This invention describes for the first time the identification of an entirely new class of compounds from cacao plant products, compounds that are not polyphenolic-based and that have biological activity. For example, this is the first detection of the presence of jasmonic acid and jasmonates in cocoa powder. In addition, the invention comprises the use of 12-hydroxy jasmonate sulfate, its isolation from cacao sources, and methods of treating and preventing disease using 12-hydroxy jasmonate sulfate and compositions comprising it.

The jasmonates are a group of naturally occurring compounds in plants that regulate growth and response to disease stress. Jasmonates, as the term is used herein, includes jasmonic acid, its esters and sulfates. Like the related prostaglandin hormones found in mammals, the jasmonates are cyclopentanone derivatives derived biosynthetically from fatty acids. They are biosynthesized from linoleic acid through the octadecanoid pathway.

As with the related compound resveratrol, jasmonates act in plants as internal signaling agents for the production of phytoalexins. Jasmonate production increases in plants due to stress and disease. The jasmonate compounds have also been identified as a new family of anti-cancer agents (Flescher, Anti-Cancer Drugs, Vol 16: 911-916 (2005); Rotem, et al., Cancer Research, Vol 65:1984-993 (2005)).

We have identified these compounds from cacao sources and identified the new compound 12-hydroxy jasmonate sulfate, using LC-MS-MS.

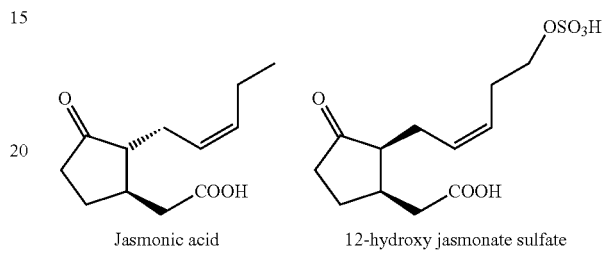

Jasmonic acid      12-hydroxy jasmonate sulfate

The invention, in one aspect, satisfies a need for beneficial jasmonate compounds in widely available consumable products, and especially products or beverages made from cocoa products. In combination with other known compounds found in cocoa, the new cocoa products, chocolates, and food ingredients and products advantageously provided by the invention create new possibilities for producing or supplementing foods with beneficial levels of natural jasmonate compounds.

In a preferred embodiment, the methods of the invention include methods of preparing a composition containing jasmonates from a cocoa product, comprising selecting cacao plant products, extracting the plant products with an organic solvent followed by aqueous solvent, and detecting the presence of 12-hydroxy jasmonate sulfate. Methods to detect jasmonates are known in the art, but a preferred method is chromatography or liquid chromatography. The cacao plant products can be: cacao beans; beans that comprise at least 10% unfermented beans; substantially all unfermented cacao beans; plant leaves; other parts of the *Theobroma cacao* plant; cocoa powder; cacao bean extracts; unfermented cacao bean extracts; a mixture of unfermented and fermented cacao bean extracts; cacao bean nibs; unfermented cacao bean nibs; fermented cacao bean nibs; and a mixture of unfermented and fermented cacao bean nibs.

In another aspect, the invention relates to methods of treating, selecting, and/or processing cacao beans or plant products to make food or cocoa ingredients, extracts, or products having improved properties or characteristics. In particular, the invention relates to methods of producing cocoa products, extracts or ingredients having desired or enhanced levels of natural jasmonate compounds, and, in particular, jasmonic acid and 12-hydroxy jasmonate sulfate. The invention also relates to novel cocoa-containing food, supplements, and beverages having enhanced levels of natural jasmonate compounds, and/or jasmonic acid or 12-hydroxy jasmonate sulfate.

It is another object of the invention to provide methods of selecting and/or processing cocoa beans for producing cocoa ingredients having enhanced levels of beneficial natural compounds. In one example, jasmonate compound levels, and, in particular, jasmonic acid or 12-hydroxy jasmonate sulfate levels are enhanced or increased.

In another aspect, the invention includes methods of analyzing a cocoa product for the presence of jasmonic acid and 12-hydroxy jasmonate sulfate, comprising selecting a cacao plant product comprising one or more of: cacao beans; chocolate liquor; cocoa powder; cocoa extract; low fat cocoa powder; defatted cocoa powder; and non fat cocoa solids; extracting the product with an organic solvent followed by an aqueous solvent, and then measuring the levels of jasmonic acid and/or 12-hydroxy jasmonate sulfate.

Cocoa ingredients having enhanced levels of jasmonates are ingredients derived from the *Theobroma cacao* plant, including beans and unfermented cacao beans, or from samples of cacao beans having more than 10% unfermented beans. Cocoa ingredients having enhanced levels of jasmonates also include ingredients derived from cocoa beans that have been treated to intentionally cause a biochemical stress in the plants, such as with UV light or by treatment with any of the other methods or combinations of methods described herein.

In particular embodiments, the invention comprises methods of enhancing the level of jasmonic acid or 12-hydroxy jasmonate sulfate present in a food product, where a sample of cacao beans is selected having about 1 µg/g or more of 12-hydroxy jasmonate sulfate, and supplementing a food product with non fat cocoa solids produced from these beans. In one aspect, the cacao beans used to produce non fat cocoa solids comprise more than 10% unfermented cacao beans. In other aspects, the cacao beans used comprise more than 10% slaty cacao beans or a mixture having more than 10% slaty and purple cacao beans. The selected beans can be made into a number of cocoa compositions, such as cocoa liquor, cocoa powder, low fat cocoa powder, defatted cocoa powder, and a cocoa extract. There are numerous food or beverage products one could make from the cocoa compositions of the invention, including but not limited to a chocolate product, a milk chocolate product, a dark chocolate product, a semisweet or bittersweet chocolate product, a chocolate-flavored product, a chocolate confectionery, a chocolate-flavored confectionery, a beverage, a chocolate beverage, a chocolate-flavored beverage, a dietary supplement, a chocolate-coated product, a low fat chocolate product, or a low-sugar chocolate product.

The invention also includes cocoa compositions that are an extract, or a food ingredient extract, made from the treated or selected beans described herein. In one aspect, the extracts of the present invention may be added to a food product or beverage without affecting the flavor, mouthfeel, or other physical or taste attributes of the food product or beverage. In another aspect, the methods of the invention may be used to make a cocoa extract from which inert and other selected compounds have been removed, such as starch, fiber, or theobromine.

In yet another aspect of the invention, the jasmonic acid or 12-hydroxy jasmonate sulfate derived from cacao plant material can be used in bioactive or pharmaceutical compositions. The jasmonic acid or 12-hydroxy jasmonate sulfate can be combined with one or more additional anti-cancer compounds, for example, such as paclitaxel, carboplatinum, and imatinib mesylate, and many others available in the art.

In the case where cacao lavado beans can be used at a medium roast, methods that preserve higher levels of jasmonate compounds could include low temperature vacuum drying up to about 85° C. product temperature, and/or optimizing the conditions for roasting of beans including choosing appropriate time, temperature and terminal moisture levels for the processed beans to result in increased levels of jasmonates. The roasting temperature is preferably no greater than 100° C. product temperature. Other methods could include steam, steam pasteurization, dry heating, dry pasteurization, chemical or physical (pressure or irradiation) treatment of the beans rendering them microbiologically safe for consumption. In so doing, the goal is to improve the yield of jasmonate compounds and/or beneficial jasmonate compounds (i.e. 12-hydroxy jasmonate sulfate, or those possessing one or more beneficial health effects as noted herein or known in the art). Thus, the invention specifically includes methods of processing cacao bean samples, especially those containing cacao lavado beans and/or other unfermented cacao beans, such as unfermented beans originating from Mexico, Guatemala or Venezuela, in order to increase or optimize the levels of jasmonate compounds, and especially 12-hydroxy jasmonate sulfate, in a resulting cocoa product compared to conventional processing methods and conventional bean samples, where the conventional methods are as described in B. Minifie, Chocolate, Cocoa, and Confectionery, 3d Ed., Aspen Publishers.

The invention also includes methods of enhancing the level of jasmonate compounds in a cocoa composition, comprising preparing a cacao bean sample having more than 10% washed, unfermented cacao beans, and processing the bean sample into a cocoa composition to produce a non fat cocoa solids-containing ingredient. More specific methods include selecting unfermented cacao beans, irradiating the beans with UV light, and preparing a cocoa composition from the beans to enhance levels. The UV treatments typically are before, during, immediately after, and/or shortly after harvesting the pods. However, UV treatments can occur at multiple steps in the process. After washing, the beans can be easily treated with UV during a drying step or a separate UV treatment step. Preferably, UV-B light or UV-C light is used, and lamps emitting UV at about 254 nm wavelength are available for these purposes. The UV light treatment can occur for about one minute, or between about 1 minute to about 15 minutes.

A further aspect of the invention is to stimulate the production of jasmonate compounds, in particular jasmonic acid and 12-hydroxy jasmonate sulfate, by taking advantage of the plant's natural ability to turn on its own disease response mechanisms by pre-exposing the cacao plant and/or its pods to inactivated pathogens or other microbes, such as non-pathogenic organisms, to trigger the plant defense systems that are known to be associated with resveratrol synthesis. For example, cocoa plants could be exposed to inactivated pathogenic bacteria or fungi, or non-pathogenic *Tricoderma* sp. or *Bacillus* sp. from about 20 to about 60 days in advance of harvesting pods to stimulate the plant disease response system and increase the level of jasmonates in the plant and pods. In a similar manner, cocoa plants could be treated with chemicals that are involved in the plant disease response system to trigger the plant's disease response system without inoculating the plant with virulent disease-causing organisms. For example, cocoa plants could be treated with salicylic acid or derivatives that are commercially available, jasmonic acid or its derivatives, or ethylene or ethreal (a commercially available spray that releases ethylene inside the plant), or other plant elicitor compounds involved in resistance to pathogens or stress. Thus, methods of the invention include treating plants to trigger the plant's own disease response systems and causing the plant to synthesize added amounts of jasmonate compounds without inoculating the plant with virulent disease-causing organisms.

In another aspect, the invention includes methods of inhibiting the enzymatic activity of COX-1 and/or COX-2 activity in cells, animals, human cells and tissue by administering an ingredient or composition having a desired level of 12-hydroxy jasmonate sulfate or jasmonic acid compounds, the ingredient prepared by selecting a sample of cocoa beans having more than 10% unfermented beans and processing the bean sample into a cocoa composition having non fat cocoa solids in an edible form. A variety of pharmaceutical compositions can be prepared by methods known or apparent to those skilled in the art and are described in more detail in, for example, Remington's Pharmaceutical Science, 17th ed., Mack Publishing Company, Easton, Pa. (1985), and the $18^{th}$ and $19^{th}$ editions thereof, which are incorporated herein by reference.

Throughout this disclosure, applicants refer to journal articles, patent documents, published references, web pages, and other sources of information. One skilled in the art can use the entire contents of any of the cited sources of information to make and use aspects of this invention. Each and every cited source of information is specifically incorporated herein by reference in its entirety. Portions of these sources may be included in this document as allowed or required. However, the meaning of any term or phrase specifically defined or explained in this disclosure shall not be modified by the content of any of the sources. The description and examples that follow are merely exemplary of the scope of this invention and content of this disclosure and do not limit the scope of the invention. In fact, one skilled in the art can devise and construct numerous modifications to the examples listed below without departing from the scope of this invention.

DETAILED DESCRIPTION OF EXEMPLARY EMBODIMENTS

In one aspect the invention involves the use of cacao beans from any source, and products made from them or derived from them. The terms "cocoa extract," "cocoa bean composition," and "cacao bean composition" can be any of a variety of products and combinations of the cacao bean-derived products noted in this disclosure. "Cocoa bean composition," "cacao bean composition" and "cocoa products" are essentially interchangeable and mean a product made from a cacao bean. A "cacao bean sample" or a "cocoa bean sample" is a collection of cacao beans or the nibs of such beans from a desired set of sources or set of processing conditions. In addition, combinations of cocoa products or cocoa extracts involving cacao beans treated, processed, or selected under conventional methods can be combined with cacao bean compositions of the invention. These compositions and extracts can be used in any cocoa ingredient, which in turn can be used in any composition or product for human consumption, including foods, confections, beverages, and supplements.

Cocoa powder, as understood in the art, contains approximately 10-25% lipid fraction (cocoa butter), which is typically retained in natural cocoa powder. However, all or a percentage of the fat can be removed from the powders by pressing, by solvent or supercritical solvent extraction or any number of other methods, as known in the art. Thus, natural, defatted and/or low fat or non-fat cocoa powders are specifically included in the cocoa products or ingredients of the invention. Other cocoa products, such as breakfast cocoa and chocolate liquor as well as dietary supplements, can also be produced from the invention.

As one of skill in the art understands, a certain amount or percentage of cocoa solids in a food ingredient can be achieved, inter alia, by using or adding an amount of cocoa powder, chocolate liquor, or other chocolate or cocoa ingredient containing the requisite amount of cocoa solids. Similarly, a certain amount or percentage of natural cocoa in a food ingredient can be achieved, inter alia, by using or adding an amount of cocoa powder, chocolate liquor or other chocolate or cocoa ingredient. In addition, while a cocoa containing product having a particular antioxidant or polyphenol level is not required, the invention encompasses the use of or combination with cocoa containing products with enhanced, altered, or increased levels of anti-oxidants or polyphenol compounds as compared to conventional cocoa containing products. Other nutritional, therapeutic, or preventative ingredients can be added as well, as known in the art.

Accordingly, in one aspect, the invention involves the novel use of unfermented cacao beans and/or collections or samples of cacao beans having certain desirable or enhanced levels of jasmonic acid or 12-hydroxy jasmonate sulfate. In particular, the cacao beans or samples of them can have about 500 ng/g or more of total jasmonates, and these beans can optionally be roasted or processed to produce a cocoa composition of the invention, such as a cocoa ingredient for a food, beverage, or supplement product. In general, the samples of cacao beans will comprise a higher level of unfermented beans than is conventionally used for cocoa processing, and samples with about 10% unfermented beans or more can lead to detectably higher 12-hydroxy jasmonate sulfate or total jasmonate levels, for example. Plants can synthesize jasmonates in response to environmental stresses, such as fungal or bacterial infections, and the fermentation process exposes cocoa beans to the stresses of high populations of microorganisms, high heat, and alcohol (See Reymond et al., Jasmonate and salicylate as global signals for defense gene expression, Current Op in Plant Biol. 1:404-411 (1998); King, et al., Bioactivity of Resveratrol, Comp. Rev. Food Sci. & Food Safety, 5: 65-70 (2006)). Collections or samples of cacao beans with 10% or more treated unfermented beans of the invention can enhance levels to a beneficial amount. Thus, combinations of beans or samples of beans that have a total jasmonates level of about 500 ng/g, or about 1 µg/g, or about 5 µg/g, or about 7 µg/g, or about 8 µg/g or more are specifically included in the invention, as well as cocoa compositions made from them, and food or consumable compositions made from them.

In another aspect, the present invention comprises cocoa ingredients having desired or enhanced levels of 12-hydroxy jasmonate sulfate and/or jasmonic acid, for example, chocolate liquor, cocoa powder, or a cocoa extract. The cocoa ingredients can be made from cocoa beans having enhanced levels of jasmonates. The term "cocoa ingredient" refers to any material containing cocoa solids that are derived from cocoa nibs. The term includes chocolate liquor, cocoa powder, cocoa extract, defatted cocoa powder, low fat cocoa powder, alkalized chocolate liquor, alkalized nibs and alkalized cocoa powder. The terms "chocolate liquor" and "cocoa liquor" refer to the viscous substance formed by grinding cocoa nibs. Chocolate liquor is the key ingredient in the manufacture of many chocolate products, for example, milk chocolate, dark chocolate, semi-sweet baking chips, reduced fat chocolate, reduced-sugar or sugar-free chocolate, chocolate-flavored coatings, and baking chocolate.

In a preferred embodiment, a cocoa powder in accordance with the present invention may have a total jasmonates content of about 500 ng/g or more, or from about 1 µg/g to about 3 µg/g to about 10 µg/g or more. A chocolate liquor according to the present invention may have a total jasmonates content of about 250 ng/g to about 1 µg/g to about 5 µg/g to about 20 µg/g or more.

In another aspect, the present invention comprises a cocoa extract having enhanced levels of natural jasmonate compounds, especially 12-hydroxy jasmonate sulfate. A cocoa extract having enhanced levels of jasmonates can be made by any method that removes the jasmonate compound(s) from the cocoa solids and fat component thus rendering it in solution. The solution can be further concentrated and the resulting extract used by itself or added to any number of foods, supplements or consumable materials.

The present invention also includes food products containing cocoa ingredients having enhanced levels of jasmonates. The term "food product" includes any edible or consumable product that can be ingested by humans or animals to provide nourishment or provide supplements, and includes but is not limited to chocolate foods, chocolate bars, chocolate candies, steeped cocoa beverages, chocolate drinks, chocolate-flavored foods, chocolate-flavored bars, chocolate-flavored candies, chocolate-flavored drinks, chocolate-coated foods, chocolate-coated bars, chocolate-coated candies, milk chocolate, dark chocolate, baking chocolate, semi-sweet baking chips, reduced-sugar chocolate and reduced-fat chocolate.

In another aspect, the invention includes ingredients or compositions, including pharmaceutical compositions, having natural jasmonate compounds derived from *Theobroma cacao*, which compounds may include jasmonic acids and 12-hydroxy jasmonate sulfate, or any other jasmonate compound occurring naturally in a cacao plant. In another aspect, the invention includes methods of inhibiting the enzymatic activities of COX-1 and/or COX-2 in cells by administering an ingredient or a composition, such as a pharmaceutical composition, having enhanced levels of natural jasmonate compounds derived from *Theobroma cacao*. The methods include administering ingredients or compositions having from about 10 mg to about 200 mg or more of 12-hydroxy jasmonate sulfate per dose in an animal.

The ingredients used in the methods may be prepared by selecting unfermented cocoa beans, or a cocoa bean sample having more than 10% unfermented beans, and processing the beans into a cocoa ingredient having non fat cocoa solids. The cocoa ingredient may be added to a food product. The compositions, including pharmaceutical compositions, may be prepared by selecting unfermented cocoa beans, reducing the beans to a powder, defatting the powder and extracting natural jasmonate compounds from the powder. The ingredients and compositions can be prepared from any part of the cacao bean. Compositions made in accordance with the present invention from the cacao shell, for example, can have higher levels of natural jasmonate compounds, such as 12-hydroxy jasmonate sulfate and jasmonic acid, than compositions prepared in other ways.

EXAMPLES

Example 1

Selecting/Producing Cacao Plant Products Having Detectable and/or Enhanced Levels of Jasmonates Cacao beans with enhanced levels of jasmonates can be selected from beans available from growers or can be produced with new treatments as disclosed here. In one example, an unfermented bean available from Mexico is used to produce a cacao plant product with detectable levels of jasmonates and to enhance 12-hydroxy jasmonate sulfate levels of cocoa compositions. Mexico cacao lavado beans are selected and washed using known methods to remove fermentable sugars. The pulp is removed and the beans are sun-dried. The dried, unfermented beans contain jasmonates and the levels of 12-hydroxy jasmonate sulfate are measured by LC-MS-MS and compared to the levels of epicatechin and proanthocyanidin A2 present. The levels of total jasmonates and of 12-hydroxy jasmonate sulfate can also be compared to standard samples, such as synthetically prepared 12-hydroxy jasmonate sulfate.

Figure 2:
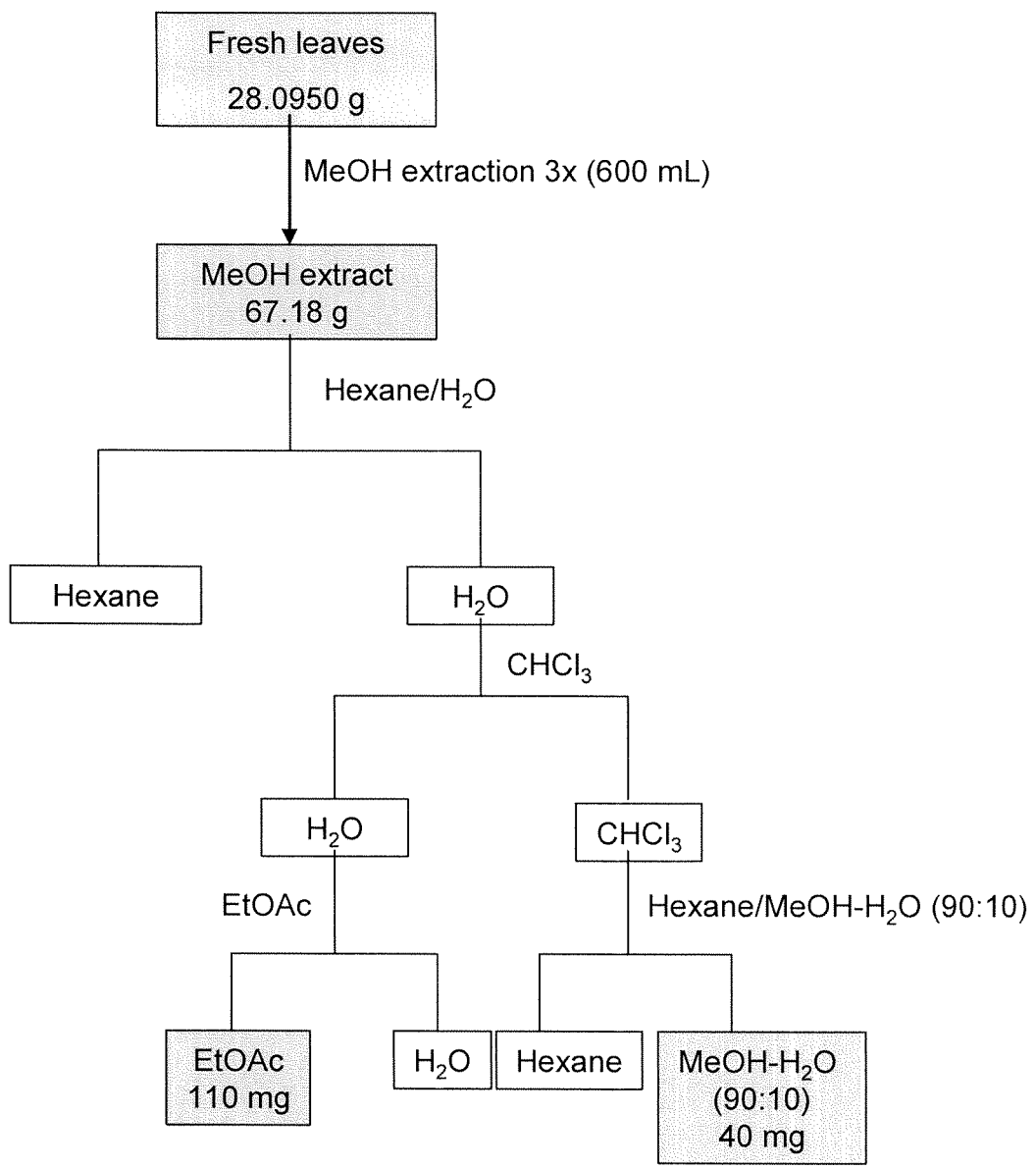
FIG. 2 depicts an exemplary extraction scheme for jasmonates and catechins from the leaves of *Theobroma cacao*.

In another embodiment, fresh leaves from *Theobroma cacao* L. are used. Sulfatases can be purchased from Sigma-Aldrich (St. Louis, Mo.). Methanol extraction is followed by defatting using hexane as shown in FIG. 2, and then ethyl acetate and methanol/water (90:10) extracts are prepared. The ethyl acetate and methanol/water extracts are then each fractionated using 018 solid phase extraction using methanol/water in the following proportions: 25:75, 50:50, 75:25, 100:0. Finally, the solid phase extraction fractions are analyzed using LC-MS.

Hydrolysis of jasmonate sulfates: A 200 µL aliquot of each cocoa extract (20 µg/mL) is incubated with 20 units of sulfatases (8.69 mg) in 200 µL sodium acetate buffer at pH 5.0 for 3, 19 or 24 h. The protein is precipitated by adding 400 µL of ethyl acetate. After removal of the protein, the desulfated jasmonate is analyzed using LC-MS.

LC-MS: The LC-MS and LC-MS-MS analyses of 12-hydroxy jasmonate sulfate are carried out using HPLC separations on Waters (Milford, Mass.) xTerra MS 018 column (21×100 mm, 3.5 µm), with a solvent system consisting of a 50 minute gradient from 95:5 to 30:70 water (containing 0.1% formic acid). The flow rate is 200 µL/min. Jasmonates and proanthocyanidins can be detected using negative ion electrospray with a Thermo Finnigan (San Jose, Calif.) TSQ Quantum triple quadrupole mass spectrometer. Proanthocyanidin A2 is detected using negative ion electrospray and the MRM transition of m/z 575 to 284.8. LC-MS-MS measurements of jasmonate sulfate utilize the abundant loss of sulfate during collision-induced dissociation, and the transition of m/z 305 to 225 (loss of sulfate from the deprotonated molecule) is monitored during LC-MS-MS using negative ion electrospray with a triple quadrupole mass spectrometer. LC-MS accurate mass measurement of the deprotonated molecule of 12-hydroxy jasmonate sulfate at m/z 305 is carried out at a resolving power of 200,000 using a Thermo Finnigan LTQ FT ICR mass spectrometer.

No epigallocatechin gallate (EGCG) is detected in the cocoa leaves. In addition, no catechin is detected in the cocoa leaves. However, catechins and jasmonate sulfate can be detected in abundance in the cocoa leaf extracts in the following order of abundance:

epicatechin>procyanidin B>quercetin glucoside>epigallocatechin>epicatechin gallate>12-hydroxy jasmonate sulfate>proanthocyanidin A2

Quantitative analyses of 12-hydroxyjasmonate sulfate in methanol extracts (0.25 mg/mL) of cocoa powder and nibs are carried out, and the results can be based on peak areas measured during LC-MS-MS. 12-Hydroxy jasmonate sulfate is detected in all cocoa and cacao nib samples. During LC-MS analysis with a high resolution FT ICR mass spectrometer (see mass chromatogram in FIG. 1), accurate mass measurement indicate a value of m/z 305.0696 which is within 0.3 ppm of the theoretical value of 305.0695 for an elemental composition of $C_{12}H_{17}O_7S$. These measurements can confirm that the elemental composition of this compound is identical to that of 12-hydroxyl jasmonate sulfate. FIG. 1 shows a negative ion LC-MS chromatogram of m/z 305 and the detection of 12-hydroxyjasmonate sulfate in cocoa powder at a retention time of 13.3 min. An accurate mass measurement can be obtained using a FT ICR mass spectrometer at a resolving power of 200,000, and the elemental composition can be confirmed to $C_{12}H_{17}O_7S$ (0.3 ppm of the theoretical mass of 305.0695).

The relative 12-hydroxy jasmonate sulfate content levels from cocoa samples and nibs is as follows:

unfermented cacao nibs (sample 2)>unfermented cacao nibs (sample 3)>cocoa extract>cocoa powder from unfermented cacao nibs>natural cocoa powder.

Example 2

Cell Culture

Several different cultured cell lines derived from cancer or tumor cells can be selected and used. For example, B16 melanoma cells, B16-F10 murine melanoma cells, Lewis lung cells, 4T1 breast tumor cells, EMT-6 breast tumor cells, Molt-4 human lymphoblastic leukemia cells, MCF7 human mammary adenocarcinoma cells, or MIA PaCa-2 human pancreas carcinoma cells can be obtained from American Type Culture Collection (ATCC, Manassas, Va.). The cells are maintained in appropriate culture, typically Dulbecco's modified Eagle medium supplemented with 10% fetal bovine serum (FBS), and additional supplements and antibiotics, such as 2 mM glutamine, 1 mM sodium pyruvate, 100 U mL$^{-1}$ penicillin, 100 g mL$^{-1}$ streptomycin and 1% nonessential amino acids. Cells are maintained in a humidified atmosphere with 5% $CO_2$ at 37° C.

Cell Viability Assay—Hoechst Cell Proliferation Assay

Although there are several methods available for the determination of cell number and proliferation, the Hoechst Cell Proliferation assay (Trivigen, Gaithersburg, Md.) provides a rapid quantitative method for measuring the absolute number of cells for both proliferating and non-proliferating cells in suspension or adherent cell culture. The assay does not require radiation or the use of toxic reagents, and is time sensitive for screening for the effects of apoptosis-modulators, cytotoxic agents, and regulators of cell division. The appropriate dye is used for adherent or suspension cultures. Cells are grown in media and washed with serum free media. Cells are resuspended in wells with serum free media and dye is added, followed by incubation for one hour. Fluorescence is measured at 355 nm and compared to control along with absolute cell number and DNA content.

The XTT cell viability assay (Biotium, Hayward, Calif.) can be employed also. Experiments can be performed in 96-well plates at about 5-10,000 cells per well. Upon completion of a desired exposure to jasmonates or control substances are a variety of concentrations for 1 to 24 hours, the XTT reaction solution is added. The solution is (sodium 3'-(1-(phenyl-aminocarbonyl)-3,4-tetrazolium)-bis(4-methoxy-6-nitro) benzenesulfonic acid hydrate and N-methyl dibenzopyrazine methyl sulfate; mixed at 50:1). The XTT reaction solution is incubated in cells in each well for 1 h at 37° C. Optical density is measured at 490 nm. Optical density is directly proportional to the number of living cells in the culture, and cytotoxicity (%) can be calculated in the following way: ((OD of control cells−OD of treated cells)/OD of control cells)×100.

Example 3

Combinations with 12-hydroxy Jasmonate Sulfate

The jasmonic acid and 12-hydroxy jasmonate sulfate compounds and compositions from cacao can be tested in the above assays and in animal trials in combination with one or more available chemotherapeutic drugs or therapeutic compounds. For example, combinations with one or more of the following: paclitaxel, adriamycin, carboplatinum, cisplatin, carboplatin, oxaliplatin, other alkylating agents, carmustine, mechlorethamine, cyclophosphamide, chlorambucil, azathioprine, mercaptopurine, irinotecan, topotecan, amsacrine, etoposide, etoposide phosphate, teniposide, dactinomycin, and steroids. Dosage levels comparable to other plant compounds, such as proanthocyanidins, can be selected, such as from about 10 to about 200 mg per dose, but other levels and multiple administrations per day can also be used.

Example 4

Cocoa Powder Having Enhanced Levels of Total Jasmonates

The total jasmonate content of a cocoa powder pressed from the cacao source of 100% unfermented Mexico lavado beans (or other unfermented cocoa beans) can be calculated. The level of jasmonates present in lavado-sourced cocoa extracts and powders is higher than those from fermented, natural cocoa powder.

Example 5

Treatments to Enhance Jasmonates During Cacao Bean Production, Harvesting or Processing The levels of jasmonic acid or 12-hydroxy jasmonate sulfate in cacao beans can be manipulated or enhanced by a number of means. Exemplary treatments or conditions for any cacao bean and in particular for unfermented cacao beans include: mold-infestation; UV irradiation; aluminum chloride treatment; aluminum sulfate treatment; ozone treatment; salicylic acid treatment; refrigerated storage; heat treatment; and any combination of these.

In one example, freshly harvested cacao beans are removed from pods, washed, and irradiated under UV-C or 254 nm wavelength light (for example, low pressure mercury 6 W lamp, or germicidal lamp) for about 1 minute, or about 1 to about 15 minutes, with optional turning to expose all sides of the bean to UV light. The UV-induction or enhancement of jasmonate levels can be examined by quantitative HPLC using common reverse phase C-18 columns and a water/acetonitrile gradient from 95/5 to 30/70.

Similarly, beans collected from pest or fungus infested pods or samples may contain higher levels of jasmonates from the disease-resistance function of the jasmonates. Many fungal infestations are known to affect *Theobroma cacao* plants, including *Moniliophthora roreri* ("Frosty Pod"), *Crinipellis perniciosa* ("Witches' Broom"), *Ceratocystis fimbriata* ("Mal de machete" or "Ceratocystic wilt"), and *Verticillium dahliae*. A preferred microbe or inoculant for this treatment is a *Botrytis* inoculant. Bean samples taken from infested plants or pods or beans intentionally infested with one or more of such fungus can be tested for levels of jasmonates compared to untreated or normal beans or plants.

Cocoa ingredients made from these beans have enhanced levels of jasmonates and can be processed to produce a cocoa extract. Extraction can be performed using an alcohol, water, hot water, ethanol, methanol, ethyl acetate, isopropanol, isopropyl alcohol, and any other aqueous or organic solvent used in the food processing industry, or a combination thereof. Chocolate liquor made from cacao beans containing more than 10% unfermented beans is reduced to cocoa powder, and the cocoa powder is defatted. The defatted powder is dried and then intermixed with desired solvent with mechanical stirring or another appropriate technique. The resulting liquid and solid portions are separated by decantation to produce a liquid extract. Cocoa extracts prepared in accordance with the invention may contain at least about 1 μg/g of total jasmonates, or at least about 10 μg/g, or 20 μg/g, or 30 μg/g, or 40 μg/g, or 50 μg/g, or 60 μg/g or more of total jasmonates. The compositions of the invention also include cocoa extracts having at least about 1 μg/mL of total jasmonates or 12-hydroxy jasmonate sulfate or jasmonic acid, or at least about 10 μg/g, or 20 μg/mL, or 30 μg/mL, or 40 μg/mL, or 50 μg/mL, or 60 μg/mL or more of total jasmonates or 12-hydroxy jasmonate sulfate or jasmonic acid. The cocoa extract may be added to a material without substantially affecting or degrading the flavor, mouthfeel, or the physical or taste attributes of the material. For example, the cocoa extract may be added to a beverage, such as a clear beverage, without changing the flavor or the visual appearance of the beverage. Alternatively, the cocoa extract may be used as a flavoring agent and dispensed from a liquid dispenser. The use of desolventizing methods, conditions, and/or compositions or solvents can also be used, for example, to improve the final characteristics or properties of the extract or a product containing it.

Other food compositions can similarly be supplemented, and an exemplary 5% amount of cocoa product from unfermented beans or jasmonate-enhanced beans as an additive can change, for example, 10% to 1% by weight of a cocoa powder from cacao lavado or unfermented beans can be used, or 7% to 5%, or 5% to 3%, or 3% to 1%, or about 2%, or about 1%. The resulting food product contains enhanced levels of jasmonates compared to conventional products of the same type.

The examples presented above and the contents of the application define and describe examples of the many cocoa compositions, products, and methods that can be produced or used according to the invention. None of the examples and no part of the description should be taken as a limitation on the scope of the invention as a whole or of the meaning of the following claims.

What is claimed is:

1. A method of enhancing the level of jasmonic compounds present in a cocoa composition used to prepare a food product or ingredient, comprising adding unfermented cacao bean nibs to a sample consisting of cocoa bean nibs so that more than 10% of the cocoa bean nibs are unfermented cacao bean nibs, pressing the sample to remove cocoa butter, processing the pressed sample into a cocoa composition having non fat cocoa solids in an edible form, and monitoring the presence of jasmonic acid or 12-hydroxy jasmonate sulfate in the sample of cocoa bean nibs.

2. The method of claim 1, further comprising extracting the sample of cocoa bean nibs with an organic solvent followed by an aqueous solvent, and detecting the presence of 12-hydroxy jasmonate sulfate.

3. The method of claim 1, wherein the cocoa composition having non fat cocoa solids in an edible form is processed into a cocoa powder.

4. The method of claim 1, wherein the cocoa composition having non fat cocoa solids in an edible form is processed into a chocolate liquor.

* * * * *